(12) United States Patent
Mulligan et al.

(10) Patent No.: US 7,130,684 B2
(45) Date of Patent: Oct. 31, 2006

(54) METHOD AND APPARATUS FOR IMPROVING VENTRICULAR STATUS USING THE FORCE INTERVAL RELATIONSHIP

(75) Inventors: Lawrence J. Mulligan, Andover, MN (US); Michael R. S. Hill, Minneapolis, MN (US); John E. Burnes, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 597 days.

(21) Appl. No.: 10/426,730

(22) Filed: Apr. 30, 2003

(65) Prior Publication Data
US 2004/0220639 A1 Nov. 4, 2004

(51) Int. Cl.
*A61N 1/362* (2006.01)
(52) U.S. Cl. ............................. 607/9; 607/24; 600/526
(58) Field of Classification Search ................ 607/1–3, 607/9, 17, 23, 24, 27, 62; 600/508–510, 600/526, 587
See application file for complete search history.

(56) References Cited

U.S. PATENT DOCUMENTS

| | | | |
|---|---|---|---|
| 5,024,222 A | 6/1991 | Thacker | |
| 5,129,394 A | 7/1992 | Mehra | |
| 5,213,098 A | 5/1993 | Bennett et al. | 128/419 |
| 5,417,717 A * | 5/1995 | Salo et al. | 607/18 |
| 5,549,650 A * | 8/1996 | Bornzin et al. | 607/24 |
| 5,564,434 A | 10/1996 | Halperin et al. | |
| 5,626,623 A | 5/1997 | Kieval et al. | |
| 6,144,880 A | 11/2000 | Ding et al. | |
| 6,213,098 B1 | 4/2001 | Kato et al. | |
| 2002/0049478 A1* | 4/2002 | Ding et al. | 607/17 |
| 2002/0115939 A1 | 8/2002 | Mulligan et al. | 600/510 |
| 2003/0074029 A1 | 4/2003 | Deno et al. | 607/23 |

FOREIGN PATENT DOCUMENTS

WO WO 03/020364 3/2003

\* cited by examiner

*Primary Examiner*—Robert Pezzuto
*Assistant Examiner*—Yun Haeng Lee
(74) *Attorney, Agent, or Firm*—Paul H. McDowall; Girma Wolde-Michael

(57) ABSTRACT

Methods and devices for improving ventricular contractile status of a patient suitably exploit changes in ventricular pressure and/or $dP/dt_{max}$ to provide and/or optimize a response to a patient. The ventricular pressure may be appropriately correlated to intracellular calcium regulation, which is indicative of contractile status. To assess ventricular contractile status, the device suitably observes a cardiac perturbation of the patient and measures force interval potentiation following the perturbation. The contractile potentiation can then be stored and/or quantified in the implantable medical device to determine the ventricular contractile status of the patient, and an appropriate response may be provided to the patient as a function of the ventricular contractile status. Examples of responses may include administration of drug or neuro therapies, modification of a pacing rate, or the like. Force interval potentiation may also be used to optimize or improve a parameter for a response provided by the implantable medical device.

37 Claims, 7 Drawing Sheets

METHOD AND APPARATUS FOR IMPROVING VENTRICULAR STATUS USING THE FORCE INTERVAL RELATIONSHIP

FIELD OF INVENTION

The invention relates to cardiac health and, more particularly, to devices and techniques for improving myocardial calcium regulation and/or ventricular contractile status.

BACKGROUND OF INVENTION

Congestive heart failure (CHF) is a widespread and seriously debilitating condition in which the heart fails to pump sufficient blood to meet the body's demand. Heart failure often results in reduced exercise tolerance, higher incidents of ventricular arrhythmia, and shortened life expectancy. It is believed that about five million Americans presently suffer from heart failure, and it is known that heart failure is the most frequent cause for hospitalization among the elderly. Heart failure costs the U.S. healthcare system approximately $38 billion annually, and this figure continues to grow as the population ages.

By tracking the contractile status of the patient's heart, the early onset of CHF can be identified and/or the progression of CHF can be monitored. Each heartbeat in a patient is triggered by a change in the calcium levels of the heart's muscle cells (called "myocytes"). More particularly, contraction and relaxation of the heart are controlled by regulation of intracellular calcium in the myocardium. As the heart ages, it generally becomes less efficiently able to pump blood, particularly during periods of exertion or exercise. This phenomenon results in part from impairment of calcium release and/or calcium uptake by the sarcoplasmic reticulum in each myocyte. Calcium regulation is therefore directly related to the contractile ability of the heart, and is a good indicator of ventricular contractile status.

Monitoring a patient's intracellular calcium regulation is therefore beneficial in diagnosing cardiac health, but tools to provide a diagnostic have not been available. Although several techniques have attempted to observe intracellular calcium regulation in the left ventricle, difficulties have arisen in practice in assessing intracellular calcium regulation for the entire heart. Further, although techniques for gauging intracellular calcium regulation have existed for some time, these techniques have been performed while the patient is undergoing an electrophysiological procedure and is not currently available for use in the ambulatory setting. As a result, patients are typically unaware of issues with the regulation of intracellular calcium in their heart. Even following admission to a emergency room, the patient is not likely to have a procedure which would provide insight into the state of intracellular calcium regulation.

Accordingly, it is desirable to create a device and/or technique that is capable of gauging intracellular calcium regulation and contractile status of the heart so that any issues can be quickly and appropriately treated. Further, it is desirable to monitor contractile status within an implantable or other device that can remain with the patient at all times.

Moreover, in a further embodiment it may be desirable to use contractile status to administer a therapy, or to provide another appropriate response to the patient or physician. Such information may also be desirably used to create a technique for optimizing the performance of a pacemaker or other implantable device.

Furthermore, other desirable features and characteristics of the present invention will become apparent from the subsequent detailed description and the appended claims, taken in conjunction with the accompanying drawings and this background of the invention.

BRIEF DESCRIPTION OF EXEMPLARY EMBODIMENTS

According to various exemplary embodiments, ventricular contractile status of a patient may be determined in an implanted medical device (IMD) by observing a perturbation of the patient's heart rate, measuring the resulting potentiation resulting from the perturbation, and quantifying the potentiation to determine the patient's contractile status. This information may be stored within the device and retrieved by a health care provider at a later time to further diagnose and/or monitor the patient's health. In a further embodiment, the patient's ventricular intracellular calcium regulation status may also be used to provide a response to the patient, such as providing an alarm and/or administering a therapy. Potentiation may be further used to tune and/or optimize a pacing parameter such as AV or VV timing intervals.

BRIEF DESCRIPTION OF DRAWINGS

Various exemplary embodiments will hereinafter be described in conjunction with the following drawing figures, wherein like numerals denote like elements, and.

DETAILED DESCRIPTION OF EXEMPLARY EMBODIMENTS

Figure 1:
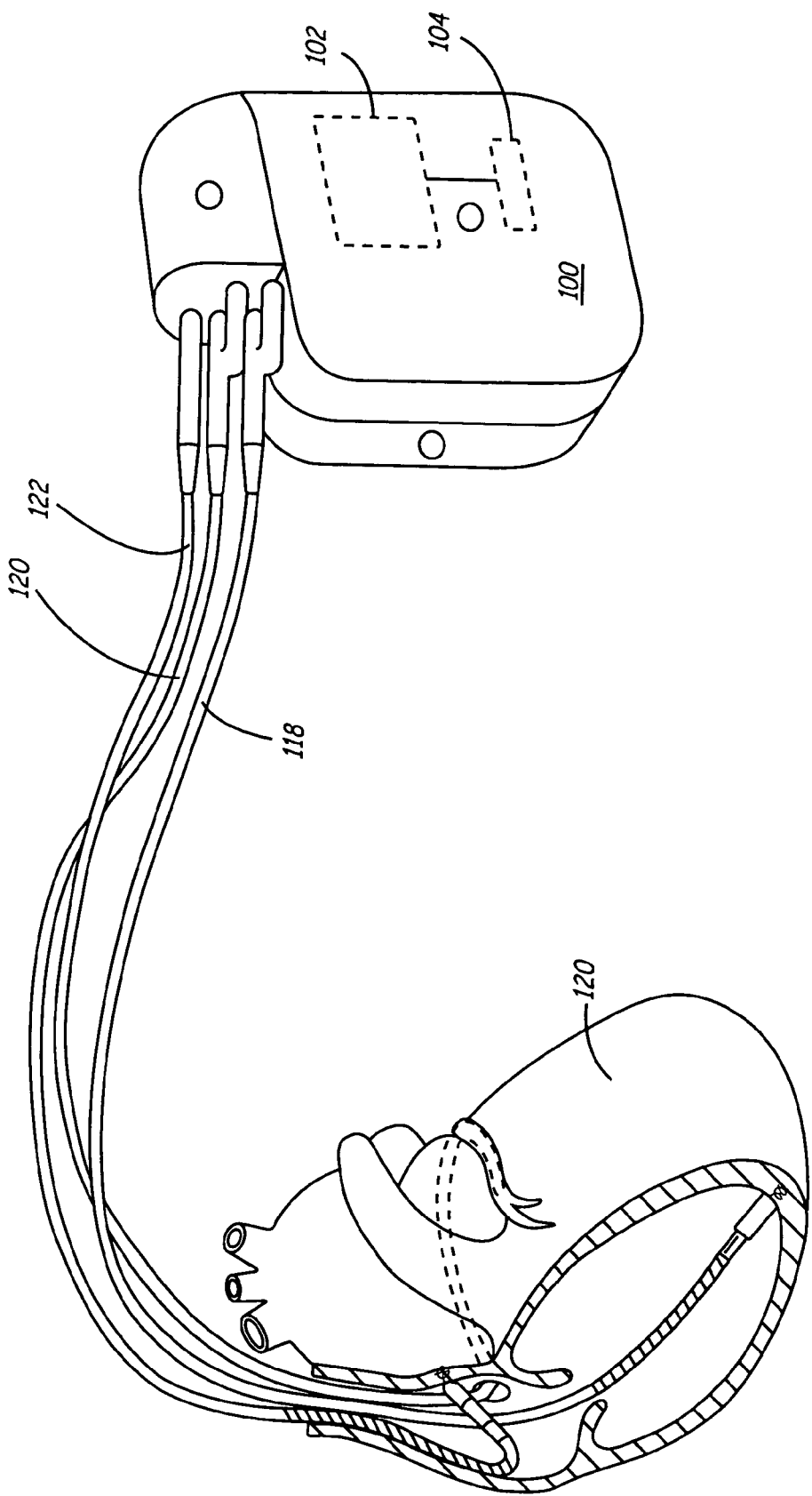
FIG. 1 is a diagram illustrating an exemplary implantable medical device in association with a patient's heart.

The following detailed description is exemplary in nature and is not intended to limit the invention or the application and uses of the invention. Furthermore, there is no intention to be bound by any theory presented in the preceding background of the invention or the following detailed description of the drawings.

As mentioned above, it has been known for some time that contraction and relaxation of the myocardium is controlled by the uptake and release of calcium from the sarcoplasmic reticulum (SR). More recently, several observers have noted that alterations in intracellular handling of calcium ($Ca^{+2}$) is associated with CHF. Changes in intracellular calcium regulation, then, can be directly correlated to the contractile status of a patient's heart, and may be indicative of the onset and/or progression of CHF and other conditions. By monitoring changes in intracellular calcium regulation, cardiac health issues can therefore be identified, monitored and treated more effectively.

One technique for evaluating SR calcium regulation involves monitoring the force-interval property of the myocardium using the contractile parameter, $dP/dt_{max}$. This quantity represents the time derivative (i.e. the rate of change) of pressure in the heart (typically in the left ventricle, although also measured in the right ventricle and elsewhere), and is known to be a good index of the force of myocardial contraction. More particularly, potentiation in dP/dt observed following a cardiac perturbation (e.g. an extra-systole, pre-mature ventricular contraction (PVC), or the like) can be quantified and tracked over time to identify changes in intracellular calcium regulation. It has been observed that premature ventricular depolarizations typically produce a relatively weak first contraction due to impairment in intracellular release of calcium. Subsequent beats, however, typically exhibit increased contractile force (i.e. potentiation) that can be measured with a ventricular pressure monitor or the like. Factors that may be monitored include the degree of systolic potentiation, as well as the time to recover from potentiation, and the like. Accordingly, the amount of potentiation following a heart beat perturbation can be a good indicator of the intracellular calcium regulation, and may provide insight into the overall hemodynamic status of the patient. In particular, measuring potentiation following a heart rate perturbation is believed to be useful in identifying patients at risk, CHF decompensation or sudden cardiac death.

The relationship between myocardial force interval and calcium regulation can be beneficially exploited in an implantable medical device (IMD) such as a pacemaker, implantable cardioverter defibrillator (ICD), or heart monitor to assess the patient's overall cardiac health. According to various embodiments, an implantable medical device (IMD) monitors potentiation resulting from a heart rate perturbation (e.g. a PVC or extrasystole) and provide information regarding the state of the patient's regulation of intracellular calcium and/or contractile status. The perturbation may be naturally occurring in the patient, or may be produced by the IMD or another appropriate device.

Data obtained at the IMD could be used for enhanced monitoring, diagnosis and/or therapeutic functions. The IMD may store diagnostic data in a memory, for example, or may activate an alarm to the patient if immediate medical attention is required, or may take other action as appropriate. In further embodiments, the IMD administers or adjusts an appropriate therapy or other response when such treatment or adjustment to the treatment is warranted. As used herein, the term "response" is intended to broadly encompass any type of medical response, alarm, report or the like (including storage of data within the IMD), as well as any of the various therapies that may be provided by the IMD to the patient. In a further embodiment, potentiation may be used to determine optimal settings for a pacing device, or for optimal delivery of a pharmaceutical or other therapy. In practice, potentiation following a cardiac perturbation can be effectively manipulated and monitored by mechanisms present in many conventional IMDs, thus making potentiation a very effective parameter for monitoring or improving a patient's cardiac health.

With reference now to FIG. 1, an exemplary implantable medical device (IMD) 100 is connected to monitor a patient's heart 120. IMD 100 may be further configured to integrate both monitoring and therapy features, as will be described below. IMD 100 suitably collects and processes data about heart 120 from one or more sources (e.g. heart rate monitor, blood pressure monitor, electrocardiogram (ECG) waveform, electrogram waveform (EGM), or more generally PQRST waveform, etc.). IMD 100 may further provide therapy or other response to the patient as appropriate, and as described more fully below. As shown in FIG. 1, IMD 100 may be generally flat and thin to permit subcutaneous implantation within a human body, e.g., within upper thoracic regions or the lower abdominal region. IMD 100 may include a hermetically-sealed housing that encloses a processor 102, a digital memory 104, and other components as appropriate to produce the desired functionalities of the device. In various embodiments, IMD 100 is implemented as any implanted medical device capable of measuring the heart rate of a patient, including, but not limited to a pacemaker, defibrillator, electrocardiogram monitor, blood pressure monitor, drug pump, insulin monitor, or neurostimulator. An example of a suitable IMD device that may be used in various exemplary embodiments is the CHRONICLE monitoring device available from Medtronic, Inc. of Minneapolis, Minn., which includes a mechanical sensor capable of detecting changes in ventricular pressure (dP/dt). In a further embodiment, IMD 100 is any device that is capable of sensing ventricular pressure and of providing pacing and/or defibrillation to the heart. Another example of an IMD capable of sensing dP/dt and other pressure-related parameters is described in commonly assigned U.S. Pat. No. 6,438,408B1, which issued to Mulligan et al. on Aug. 20, 2002.

Processor 102 may be implemented with any type of microprocessor, digital signal processor, application specific integrated circuit (ASIC), field programmable gate array (FPGA) or other integrated or discrete logic circuitry programmed or otherwise configured to provide functionality as described herein. Processor 102 executes instructions stored in digital memory 104 to provide functionality as described below. Instructions provided to processor 102 may be executed in any manner, using any data structures, architecture, programming language and/or other techniques. Digital memory 104 is any storage medium capable of maintaining digital data and instructions provided to processor 102 such as a static or dynamic random access memory (RAM), or any other electronic, magnetic, optical or other storage medium.

As further shown in FIG. 1, IMD 100 may receive one or more cardiac leads for connection to circuitry enclosed within the housing. In the example of FIG. 1, IMD 100 receives a right ventricular endocardial lead 118, a left ventricular coronary sinus endocardial lead 122, and a right atrial endocardial lead 120, although the particular cardiac leads used will vary widely from embodiment to embodiment. In addition, the housing of IMD 100 may function as an electrode, along with other electrodes that may be provided at various locations on the housing of IMD 100. In alternate embodiments, other data inputs, leads, electrodes and the like may be provided. Ventricular leads 118 and 122 may include, for example, pacing electrodes and defibrillation coil electrodes (not shown) in the event IMD 100 is configured to provide pacing, cardioversion and/or defibrillation. In addition, ventricular leads 118 and 122 may deliver pacing stimuli in a coordinated fashion to provide biventricular pacing, cardiac resynchronization, post-extrasystolic potentiation (PESP) therapy or other benefits. Exemplary PESP therapy includes those described in U.S. Pat. No. 6,213,098 to Bennett et al. and non-provisional U.S. patent application Ser. No. 10/xxx,xxx to Deno et al. filed on 28 Aug. 2002, the contents of both disclosures are hereby incorporated by reference herein. IMD 100 may also obtain input data from other internal or external sources (not shown) such as a ventricular pressure monitor, pH monitor, arterial pressure monitor, accelerometer or the like.

In operation, IMD 100 suitably obtains data about heart 120 via leads 118, 120, 122, and/or other sources. This data is provided to processor 102, which suitably analyzes the data, stores appropriate data about the episode in memory 104, and/or provides a response or report as appropriate. Any identified cardiac episodes (e.g. an arrhythmia or heart failure decompensation) can be treated by intervention of a physician or in an automated manner. In various embodiments, IMD 100 activates an alarm upon detection of a cardiac episode. Alternatively or in addition to alarm activation, IMD 100 selects or adjusts a therapy and coordinates the delivery of the therapy by IMD 100 or another appropriate device. Optional therapies that may be applied in various embodiments may include drug delivery, electrical stimulation, neurostimulation, modifications in pacing rate, and/or the like.

Figure 2:
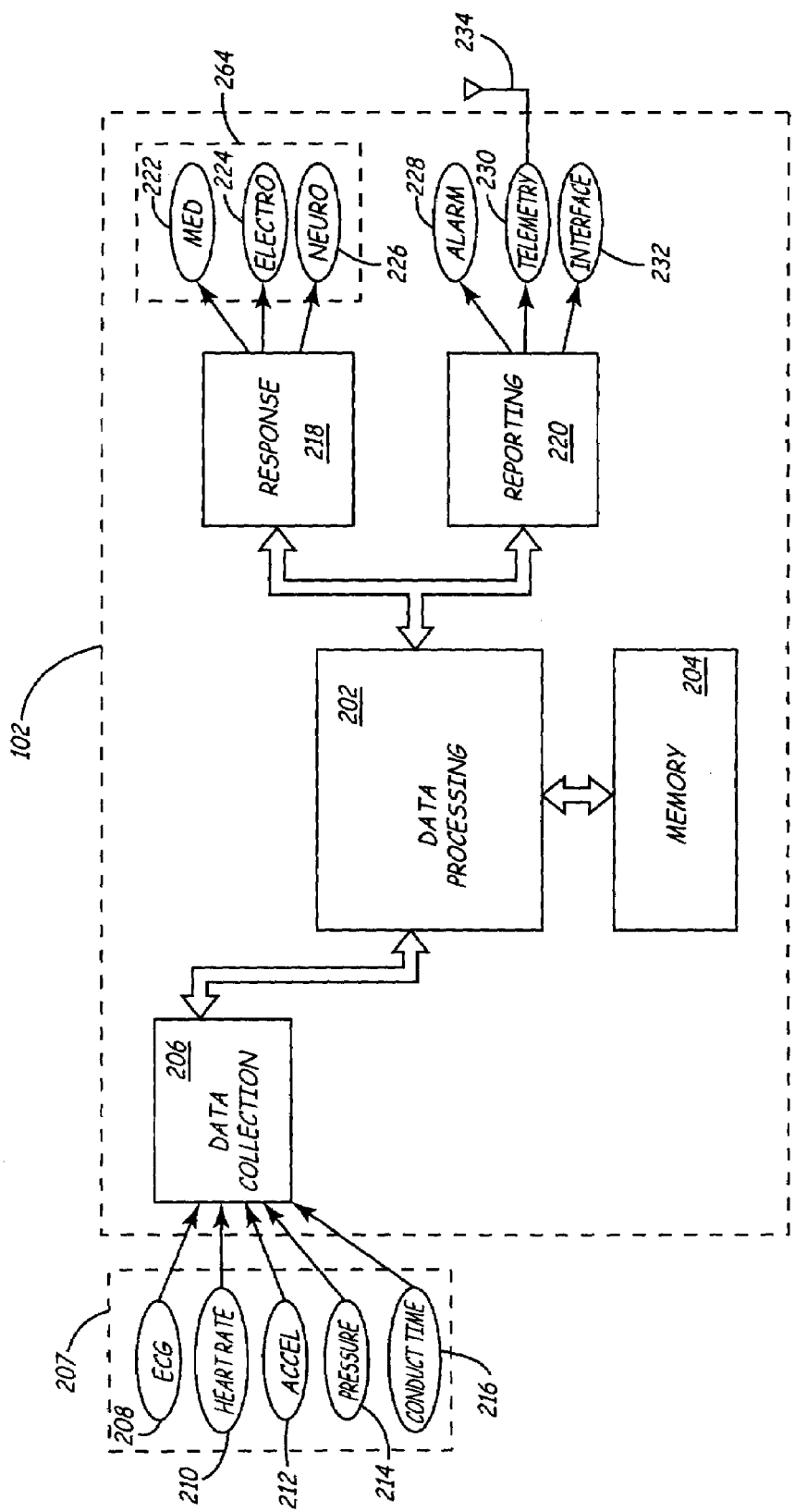
FIG. 2 is a conceptual block diagram showing exemplary processing modules for an implantable medical device.

With reference now to FIG. 2, an exemplary data processing layout for an IMD 100 suitably includes a data collection module 206, a data processing module 202, a response module 218 and/or a reporting module 220. Each of the various modules may be implemented with computer-executable instructions stored in memory 104 and executing on processor 102 (FIG. 1), or in any other manner. The exemplary modules and blocks shown in FIG. 2 are intended to illustrate one logical model for implementing an IMD 100, and should not be construed as limiting. Indeed, the various practical embodiments may have widely varying software modules, data structures, applications, processes and the like. As such, the various functions of each module may in practice be combined, augmented, optimized or otherwise differently-organized in any fashion.

Data collection module 206 suitably interacts with one or more data sources 207 to obtain data about the patient. Data sources 207 include any source of information about the patient's heart, blood, temperature and/or the like. In various embodiments, data sources 207 include an ECG or EGM source 208 that provides electrical impulses or other observed signals that can be used to model the patient's electrocardiogram (ECG) waveform. Other data sources 207 may include a heart rate sensor 210, a ventricular pressure monitor 214, an accelerometer 212, a sensor 216 for determining cardiac conduction time and/or the like. The various data sources 207 may be provided alone or in any combination with each other, and may vary widely from embodiment to embodiment. Sensors for cardiac conduction time 216 and heart waveform 208 data could be combined into a single pair of electrodes, for example. Moreover, other data sources 207 such as temperature sensors, blood pH sensors or the like could additionally or alternatively be provided. One example of a pressure sensor 214 is described in commonly assigned U.S. Pat. No. 5,564,434.

Data collection module 206 suitably receives data from each of the data sources 207 by polling each of the sources 207, by responding to interrupts or other signals generated by the sources 207, by receiving data at regular time intervals, or according to any other temporal scheme. Data may be received at data collection module 206 in digital or analog format according to any protocol. If any of the data sources generate analog data, data collection module 206 suitably translates the analog signals to digital equivalents using any form of analog-to-digital conversion scheme presently known or subsequently developed. Data collection module may also convert data from protocols used by data sources 207 to data formats acceptable to data processing module 202, as appropriate.

Data processing module 202 is any circuit, programming routine, application or other hardware/software module that is capable of processing data received from data collection module 206. In various embodiments, data processing module 202 is a software application executing on processor 102 (FIG. 1) to implement the process described below in conjunction with FIG. 3. Accordingly, data processing module 202 suitably interprets received ventricular pressure (i.e. dP/dt) or other data to quantify potentiation or other effects in the patient's cardiac status and to produce an appropriate response, as described more fully below.

Issues in the patient's cardiac health can be detected, for example, when the amount of potentiation in $dP/dt_{max}$ deviates from a baseline reading by more than a threshold amount, or according to any other criteria. The baseline amount of potentiation may be a static value, or may be updated over time. In various embodiments, the baseline data represents a mean or median value observed over any appropriate number of preceding samples. Threshold values may be any nominal values derived from a typical population of patients, or from any other source. Alternatively, the threshold values may be independently adjusted and set for a given patient as desired by the attending physician. In various embodiments, the more recent values of potentiation, as well as other information, may be stored in a memory 204 to facilitate diagnosis of the patient. In another embodiment, data values observed during a particular time period or near a cardiac event deemed important by algorithms in the IMD (e.g. preceding an observed arrhythmia) may be stored in a memory 204 to facilitate diagnosis of the patient.

In an exemplary embodiment, processing module 202 receives ventricular pressure data 214 and/or other appropriate information from data collection module 206 and interprets the data using conventional digital signal processing techniques. If a heart beat perturbation occurs, data about the episode (e.g. the duration and/or magnitude of potentiation, time and date of the episode, and/or the like) may be stored in memory 204, which may correspond to hardware memory 104 shown in FIG. 1, or may be implemented with any other available digital storage device.

When a perturbation is identified, processing module 202 may trigger an appropriate response if warranted by the data resulting from the perturbation. Responses may be activated by sending a digital message in the form of a signal, passed parameter or the like to response module 218 and/or reporting module 220.

Reporting module 220 is any circuit or routine capable of producing appropriate feedback from the IMD to the patient or to a physician. In various embodiments, suitable reports might include storing data in memory 204, generating an audible or visible alarm 228, producing a wireless message transmitted from a telemetry circuit 230 via an antenna 234, or providing other data that may be downloaded from a serial, parallel or other interface 232. Reports may include information about the potentiation duration and/or magnitude, time and date of episode occurrence, or any other appropriate data. In a further embodiment, the particular response provided by reporting module 220 may vary depending upon the severity of the episode. Minor episodes may result in no alarm at all, for example, or a relatively non-obtrusive visual or audible alarm. More severe episodes might result in a more noticeable alarm, in addition to an automatic response as described below.

Telemetry circuitry 230 communicates data from IMD 100 to an external device via antenna 234. The external device receiving the wireless message may be a programmer/output device that advises the patient, a physician or other attendant of serious conditions, e.g., via a display or a visible or audible alarm. Information stored in memory 204 may be provided to an external device via antenna 234 for example, to aid in diagnosis or treatment of the patient. Alternatively, the external device may be an interface to a telephone network such that IMD 100 is able to automatically notify emergency personnel if an extreme episode occurs.

Interface 232 is any serial, parallel or other interface to an external computing device. Interface 232 and/or telemetry circuit 230 may be used to provide information from IMD 100 to an external device. Information stored in memory 204 may be provided to an external digital computer or other device, for example, to aid in diagnosis or treatment of the patient.

Response module 218 is any circuit, software application or other component that interacts with any type of therapy-providing system 264, which may include any type of therapy deliver mechanisms such as a drug delivery system 222, neurostimulation 226 and/or cardiac stimulation 224. In some embodiments, response module 218 may alternatively or additionally interact with an electrical stimulation therapy device integrated with IMD 100 to deliver pacing, post-extrasystolic potentiation, cardioversion, defibrillation and/or any other therapy. Accordingly, the various responses that may be provided by IMD 100 vary from simple storage of data to actual provision of therapy in various embodiments. Any therapy provided may be titrated or otherwise adjusted in response to potentiation observed, as described more fully below. Drug dosage may be adjusted according to episode severity, for example, or pacing parameters can be adjusted in response to observed potentiation.

The various components and processing modules of IMD 100 may be housed in a common housing such as that shown in FIG. 1. Alternatively, portions of IMD 100 may be housed separately. For example, portions of the therapy delivery system 264 could be integrated with IMD 100 or provided in a separate housing, particularly where the therapy delivery system includes drug delivery capabilities. In this case, response module 218 may interact with therapy delivery system 264 via an electrical cable or wireless link, or via interface 232.

Figure 3A:
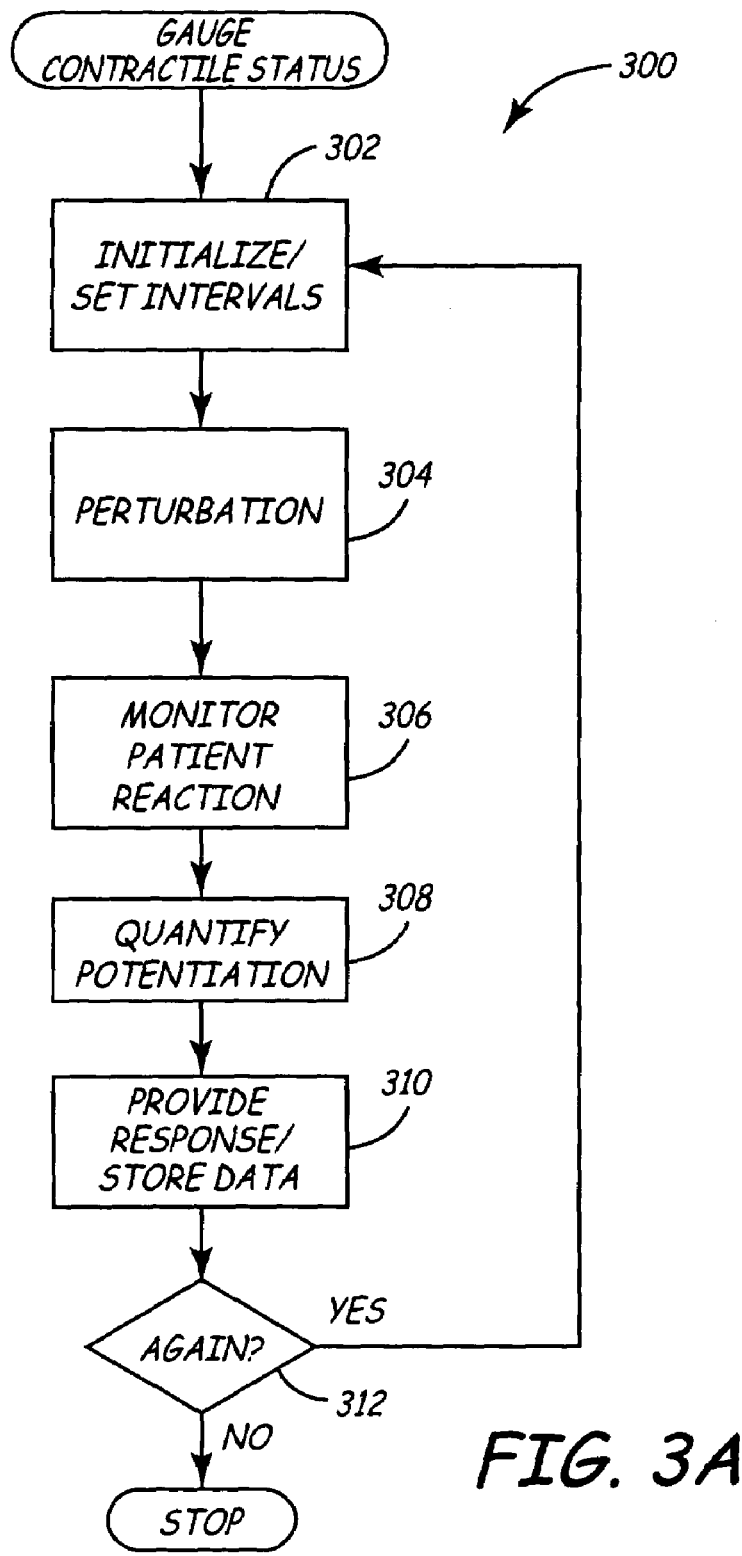
FIG. 3A is a flowchart of an exemplary process for gauging a patient's contractile status that may be executed within an implantable medical device.

With reference now to FIG. 3, an exemplary process 300 for gauging the contractile status of a patient suitably includes the broad steps of generating and/or observing a heart rate perturbation (step 304), measuring the associated potentiation generated by the perturbation (step 306), and processing or quantifying the data to correlate the potentiation with the patient's intracellular calcium regulation, ventricular contractile status and/or cardiac health (step 308). In various embodiments, the various steps of process 300 may be implemented with computer-executable instructions that are stored in a digital memory 104 and that are appropriately executed by processor 102 (FIG. 1), or by any other processor associated with the IMD.

Process 300 suitably begins by setting appropriate pacing intervals by IMD and/or otherwise initializing the IMD for the gauging process (step 302). An exemplary technique for determining optimum pacing intervals is set forth below in conjunction with FIG. 5, although any steady state pacing routine could be used in alternate embodiments. Initialization may also include setting or resetting any counters, timers or other variables within processor 102 as appropriate. After pacing intervals are set, it may be desirable to maintain the pacing state for a short period of time (e.g. on the order of thirty seconds or so) to allow the patient's hemodynamics to settle into a relatively steady state. In a further embodiment, process 300 may be performed when the patient is asleep or at rest to further minimize transient effects upon the heart. Periods of sleep or rest may be identified by a clock in IMD 100, by a manual activation, by accelerometer data (e.g. accelerometer 212 in FIG. 2), or by any other technique. Likewise, process 300 may be withheld when the patient is active or extremely active, or otherwise has a high heart rate, as appropriate.

Analysis of potentiation suitably begins by identifying a perturbation to the patient's heart such as a PVC or other change the heartbeat that results in a change in the patient's hemodynamics. Various forms of cardiac perturbations may include any ventricular beat originating from a different source than a baseline beat, or that produces a smaller or larger output from the heart. Perturbations may be naturally-occurring, or may be initiated by IMD 100 as described more fully below. A perturbation may be generated, for example, by inducing a premature beat in either ventricle, and/or by adjusting the rate at which either the left and/or right ventricle are paced. In the context of baseline ventricular pacing, for example, changes in hemodynamic pressure can be induced in the patient by pacing a single ventricle for one or more beats.

In an exemplary embodiment, naturally-occurring perturbations (e.g. PVCs) in the patient are identified by monitoring electrocardiogram (ECG) data such as a PQRST waveform or the like within IMD 100. Data may be collected according to any scheme, but in an exemplary embodiment data measurements are taken at regular time intervals with a sufficiently high frequency to identify any natural perturbations of the patient's heart rate. Although an exemplary process 300 discussed herein emphasizes monitoring dP/dt for purposes of simplicity and illustration, other equivalent data factors such as atrial and/or ventricular pressure may be used in addition to or in place of dP/dt data in various alternate but equivalent embodiments. In a further exemplary embodiment, perturbations following unusual conditions may be ignored or differently processed by IMD 100, as discussed below, so that the patient's condition can be monitored over time under relatively constant conditions.

In an alternate embodiment, IMD 100 induces extrasystolic beats (atrial or ventricular), PVCs and/or other cardiac perturbations so that the patient's reactions can be appropriately monitored and/or tested. In such embodiments, IMD 100 suitably provides pacing to the heart prior to the premature beat to place the heart into a steady rhythmic state, as described above. Further, IMD 100 may provide a string of extrastimuli entrainment beats (e.g. S1 beats) immediately prior to the premature beat to further place the heart into a known state. In an exemplary embodiment, a train of S1 beats having a pacing rate roughly equal to the intrinsic rate may be provided by IMD 100, followed by a premature S2 beat at a rate of about forty percent to about sixty percent of the S1 rate, followed in turn by a train of S3 beats having approximately the same rate as the S1 beats preceding the premature beat. Of course, any combination of S1, S2, S3, S4 and/or other beats at any pacing rate or prematurity could be used in alternate embodiments, and the particular rates used for each pulse could be adjusted accordingly. The S1 and S3 beats, for example, could be provided at a rate that is slightly (e.g. about ten percent) faster than the intrinsic rate in an alternate embodiment. Again, cardiac perturbations observed within step 304 may be naturally-occurring and/or induced by IMD 100 or another device in any manner.

When a perturbation is identified, the patient's reaction to the perturbation is observed and/or recorded (step 306). The reaction may be observed by monitoring data from a pressure sensor 214 (FIG. 2) to determine the magnitude and/or duration of any resulting potentiation. In an exemplary embodiment, $dP/dt_{max}$ data is obtained for either or both ventricles. Data may be gathered for any interval of time or for any number of beats, or for any other duration. In an exemplary embodiment, data is gathered for about twenty beats following the perturbation, or until the heart returns to its original pre-perturbed state. Data gathered is stored in memory 104 (FIG. 1) or another appropriate location for processing by IMD 100. Data gathered prior to the perturbation may also be stored within memory 104, or elsewhere on IMD 100.

In various embodiments, it may be desirable to analyze the patient's condition under relatively constant conditions over time. Variations in the perturbation may therefore create inconsistent data that may be of reduced benefit. To avoid this situation, in certain embodiments IMD monitors the patient's heart beat cycle length, coupling intervals and/or other parameters prior to the perturbation so that perturbations resulting from unusual baseline conditions may be flagged or otherwise differently processed. If a patient experiences PVCs following coupling intervals of 500 ms, 550 ms and 800 ms, for example, analysis of the 800 ms PVC may be ignored or separated from the analysis of the other PVCs in various embodiments. Accordingly, certain embodiments may ignore or otherwise differently-process perturbations that occur following unusual or non-standard conditions.

After data is gathered, the stored data is processed to quantify the potentiation experienced by the patient and to correlate the potentiation to the patient's intracellular calcium regulation status and/or ventricular contractile status. Potentiation may be quantified according to any process or technique, including evaluation of recirculation fraction, potentiation ratio, and/or any other parameter related to changes in dP/dt following a perturbation to the heart.

Figure 3B:
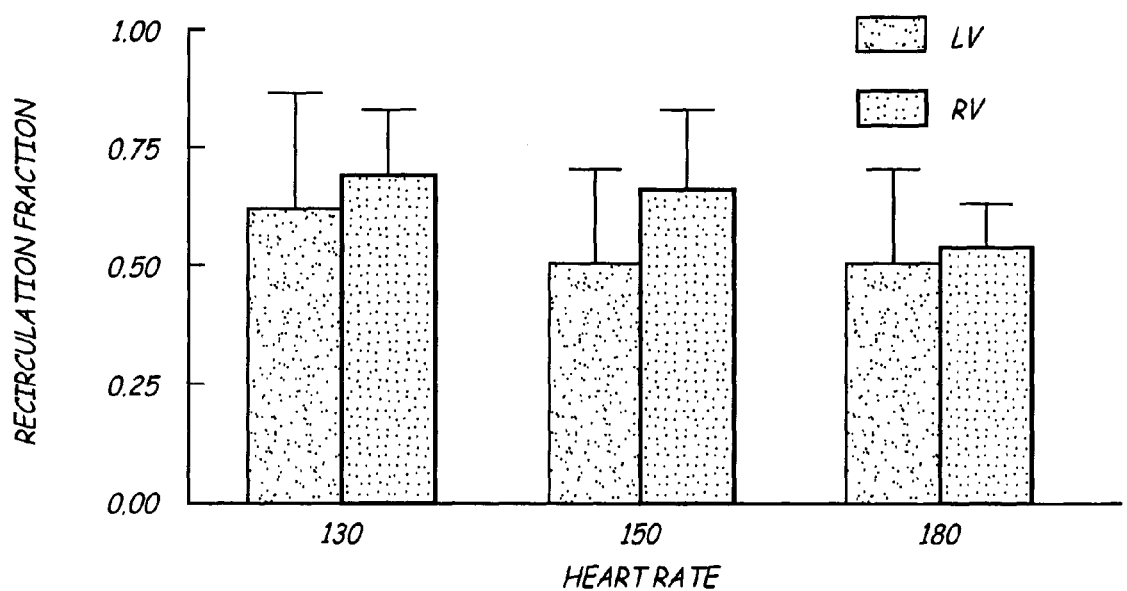
FIG. 3B is an exemplary plot of observed values for recirculation fraction in the left and right ventricles for various heart rates.

Recirculation fraction (RF) is considered to be the ratio of calcium ($Ca^{+2}$) released from the sarcoplasmic reticulum that is re-sequestered back on the SR on each beat. Because calcium re-uptake is known to be linearly related to the force-interval property of the myocardium, however, RF may be derived from the recovery of potentiated beats following the perturbation, although other techniques could be used in alternate embodiments. FIG. 3B shows an exemplary plot of RF measurements in both the left and right ventricles following an extra-systole at 320 msec for several different heart rates. As can be seen in FIG. 3B, no significant difference was observed between the left and right ventricular RF for each respective heart rate. Similarly, RF is believed to be only minimally influenced by the extra-systolic interval, making RF a convenient and effective parameter for evaluating calcium regulation in the heart.

Figure 3C:
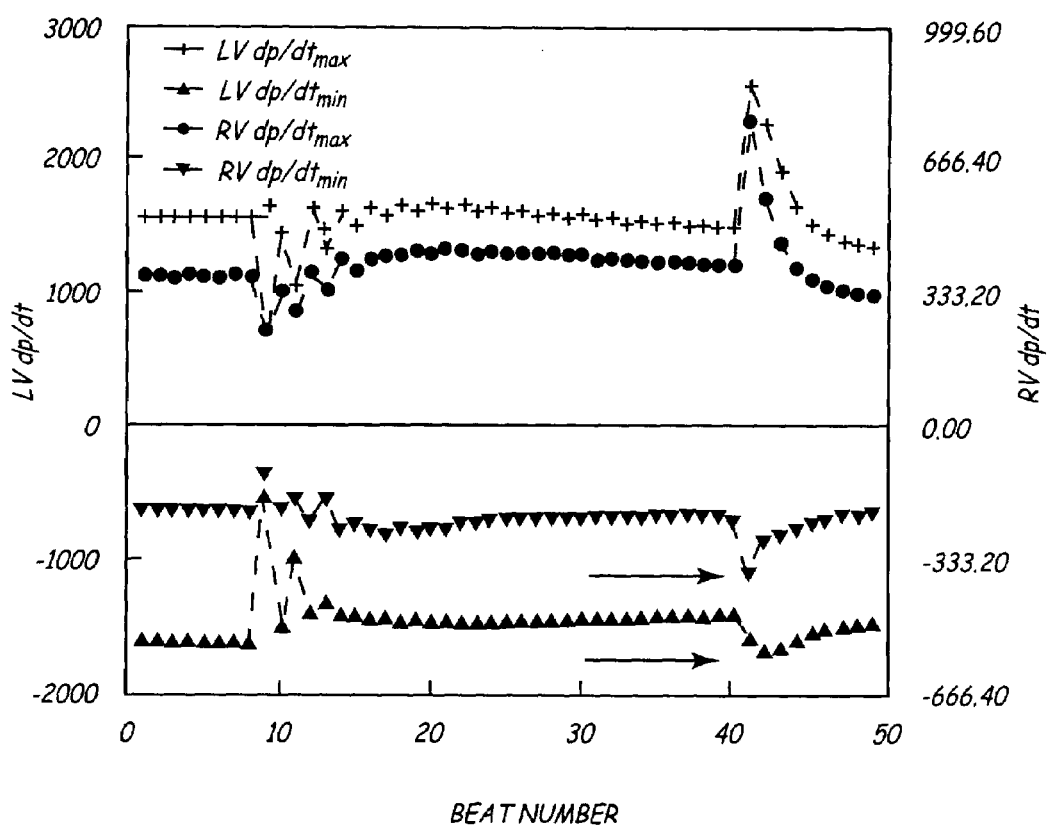
FIG. 3C is an exemplary plot of observed values for potentiation ratios observed in left and right ventricles.

While recirculation fraction focuses primarily on systolic recover, however, additional or alternative parameters may be measured to describe both systolic and diastolic function. The potentiation ratio (PR), for example, conventionally provides a ratio of the force at the greatest level of potentiation to the force in response to the last priming beat. Stated another way, PR may be determined by comparing the potentiation from one or more beats following the perturbation to the mean of the control beats prior to the perturbation. PR may also be evaluated following an abrupt decrease in heart rate, as shown in FIG. 3C.

Equivalent time-based techniques for quantifying potentiation include measuring the time for the $dP/dt_{max}$ to return to a normal level following the perturbation, or measuring the time from the perturbation to a minimum or maximum dP/dt observed in a window of time following the perturbation. Accordingly, PR may be used alone or in conjunction with RF and/or other parameters to monitor intracellular calcium regulation, which in turn correlates to ventricular contractile status.

Potentiation data (e.g. RF, PR and/or the like) may be correlated to a patient's hemodynamic condition or overall cardiac health in any manner. Generally speaking, greater amounts of potentiation following a perturbation are considered to be more favorable than lesser values, since the greater amount generally indicates better intracellular calcium regulation. As discussed more fully below, data may be stored within IMD 100 to track changes over time. Extremely low amounts of potentiation may provoke IMD 100 to issue an alarm or warning for the patient to seek medical attention, and/or IMD 100 may use potentiation to process an additional response (step 310) such as administering a drug, neurological or other therapy, or to adjust pacing rates or other parameters. Process 300 may be executed repetitively (step 312) to maintain data over time, or to iteratively adjust a therapy or other parameter. In such embodiments, therapies may be applied in a "closed loop" manner, whereby continuous monitoring of the patient's condition is provided as feedback to drive application and/or adjustment of one or more therapies. Neurostimulation or other treatments, for example, may be applied in such magnitudes and durations as appropriate to bring the patient's cardiac condition back to normal, or to improve the condition. In such embodiments, potentiation or other parameters can be monitored and/or titrated in a "closed loop" manner using conventional control techniques until the parameter reaches a desired value.

Figure 4:
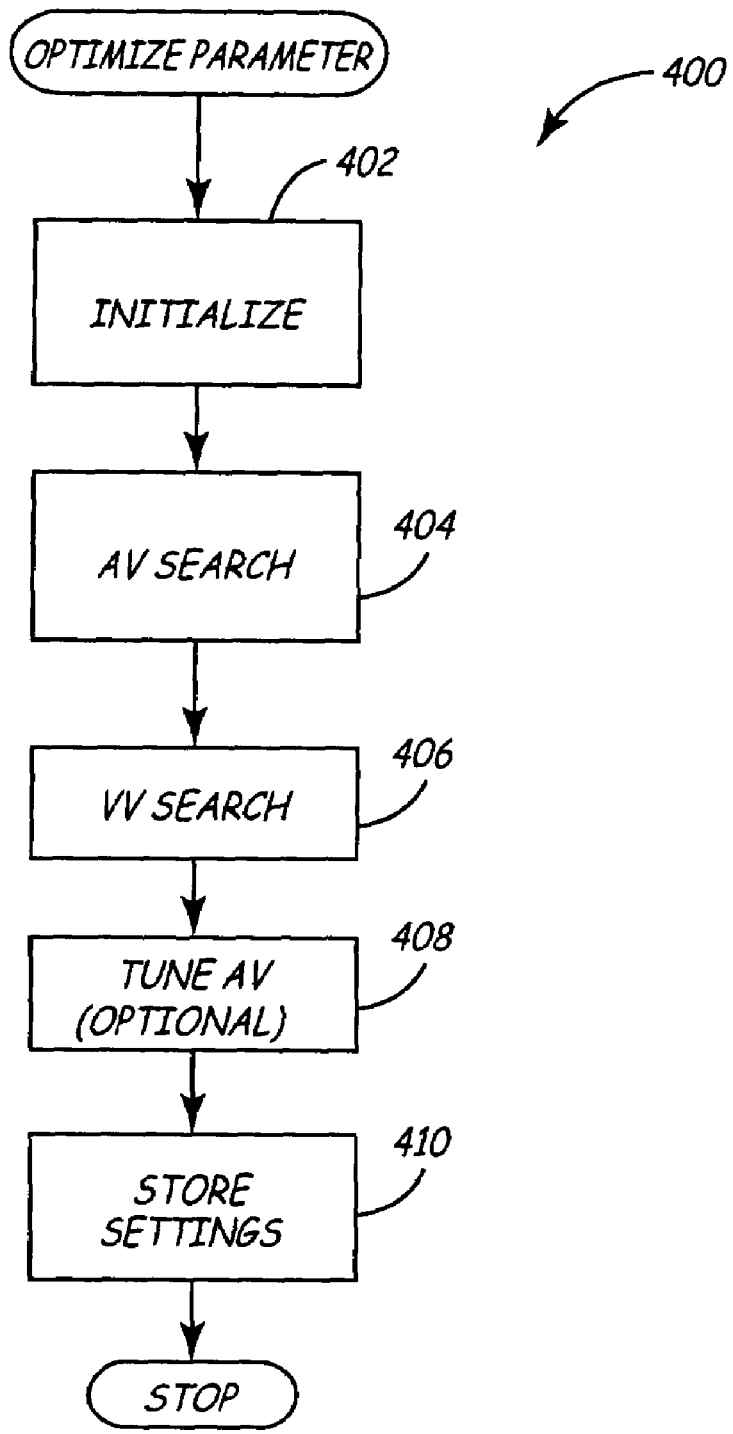
FIG. 4 is a flowchart of an exemplary process for optimizing timing parameters and/or therapy application as a function of ventricular force interval.

Potentiation observations following a perturbation may be used to optimize therapy parameters within a pacemaker or other implantable device 100 capable of delivering therapy. With reference now to FIG. 4, an exemplary process 400 for optimizing pacing parameters suitably includes the broad steps of setting initial pacing parameters to be evaluated (step 402), adjusting one parameter (e.g. the atrial-ventricular (A-V) interval) (step 404), adjusting a second parameter (e.g. the cross-ventricular (V-V) interval) (step 406), optionally re-visiting the first parameter (e.g. A-V interval) (step 408), and storing the optimal settings (step 410) for continued operation of IMD 100. The various steps of process 400 may be implemented with computer-executable instructions stored in a digital memory 104 and that are appropriately executed by processor 102 (FIG. 1), or by any other processor associated with IMD 100.

Initial pacing parameters (step 402) may be set to any convenient initial value as determined from statistical models, historical data, patient history, physician input or any other source. In an exemplary embodiment, initial pacing intervals may be about 100 ms for A-V interval and about 0 ms for V-V interval, although any other intervals could be used. Optimization of pacing intervals takes place using any suitable technique, such as the iterative technique described below in conjunction with FIG. 5. Generally speaking, IMD 100 gradually modifies the pacing parameters while monitoring potentiation resulting from the changes. Because high potentiation generally correlates to better calcium regulation, the parameter that produces the highest amount of potentiation may be deemed to be optimal for continued pacing. After an optimal parameter for one type of pacing (e.g. A-V pacing) is identified, that setting can be used during optimization of another pacing parameter. After both parameters have been optimized, various embodiments include cross-checking of the first parameter (step 408) so that the optimal pacing parameters for both types of pacing are evaluated together. Although FIG. 4 shows A-V interval evaluation (step 404) as taking place prior to V-V interval evaluation (step 406), the respective order may be altered such that V-V intervals are optimized prior to A-V intervals, with any follow-up V-V optimization taking place after an optimal A-V interval is determined.

Figure 5:
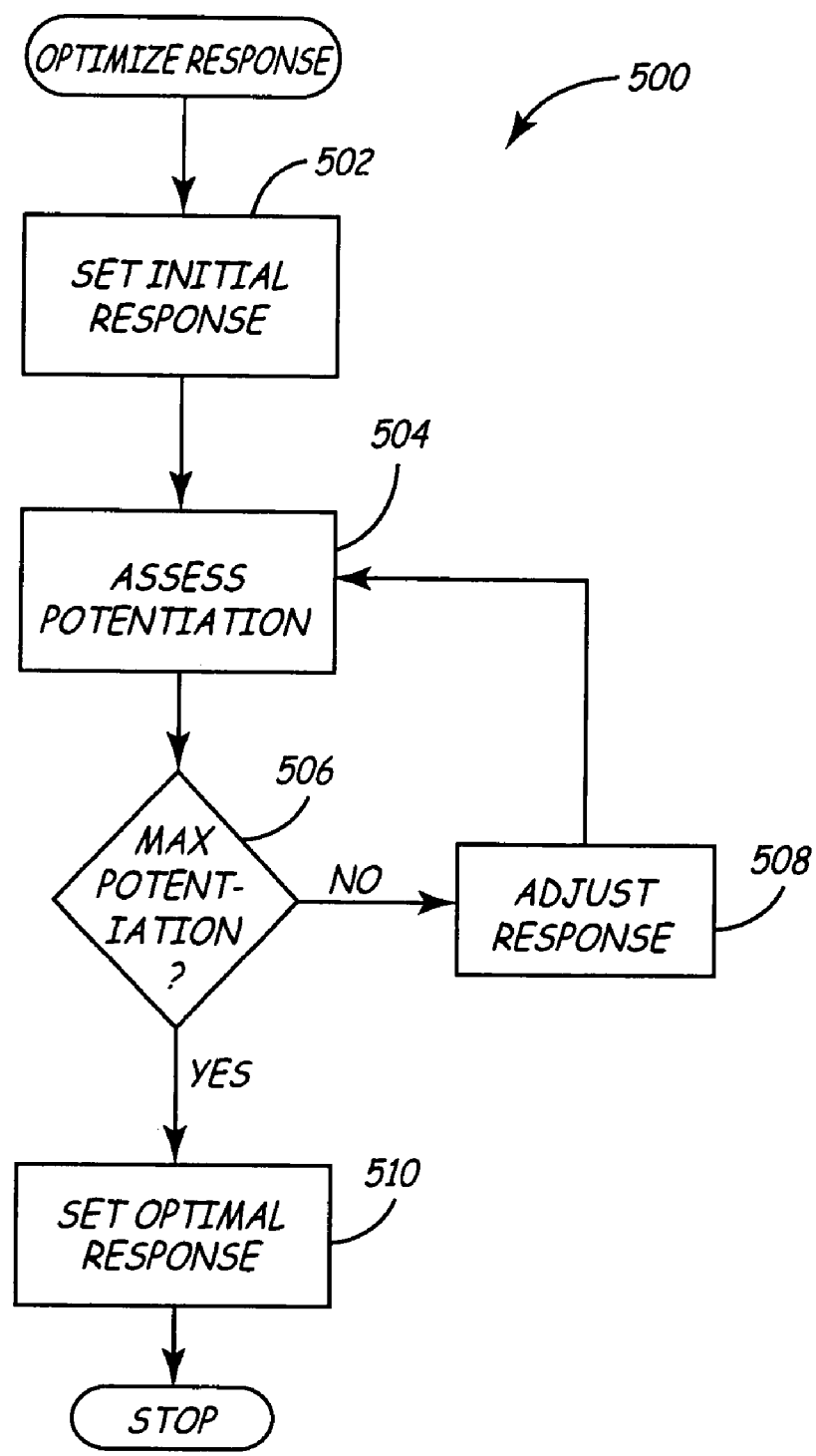
FIG. 5 is a flowchart of an exemplary process for tuning a response generated by an implanted medical device as a function of ventricular force interval.

With reference now to FIG. 5, an exemplary process 500 for optimizing a response from an IMD 100 suitably includes iteratively providing a response (step 502), determining the potentiation produced by the response (step 504), and adjusting the response (step 508) until an optimal (e.g. a maximum) potentiation is identified. Responses that may be optimized in various embodiments include pacing parameters, administration of drug or neuro-therapies, or the like. As with the processes described above, the various steps of process 500 may be implemented with computer-executable instructions stored in a digital memory 104 or other storage medium and executed by any processor 102 associated with IMD 100.

To begin the optimization process, a baseline response is initially provided from IMD 100 (step 502). Baseline responses may be obtained from historical data, patient history, physician input, or any other source. For example, to optimize A-V intervals, the baseline AV interval may be initially set at about 100 ms with no V-V delay. Once the AV interval is optimized, the V-V interval optimization may begin with an interval of about 0 ms, with the A-V interval set at the optimal level previously determined, for example, in step 404 of FIG. 4. Baseline levels of drug or neuro-stimulation therapy could alternatively be provided.

As the initial response from IMD 100 is applied, the patient's potentiation is observed (step 504) using the techniques described above in conjunction with FIG. 3 as appropriate. Potentiation may be quantified using PR, and/or any other parameter, for example, to determine the patient's reaction to the initial therapy. After the initial response is processed, IMD 100 suitably varies the response provided (step 508) to obtain additional data points for comparison (step 506). As mentioned above, increased potentiation generally correlates to improved hemodynamic condition, at a given extra-systolic interval, so process 500 generally seeks to maximize the level of potentiation in the patient (step 506). The observed value for each iteration is suitably maintained in IMD 100 for comparison against subsequent observations. In an embodiment that seeks to optimize A-V intervals, for example, potentiation observations may be obtained for A-V intervals of 80 ms, 100 ms, 120 ms or the like. If the maximum potentiation is produced at 120 ms, further data may be collected at 130 ms or so until a maximum value is identified. If the maximum potentiation is produced at 100 ms, the response may be adjusted to, say, 90 ms and/or 110 ms to isolate a maximum value. Further iterations may provide improved resolution, thus resulting in a more accurate optimal value produced. Of course other embodiments will use widely varying values, and the particular parameters used in this illustrative example are not intended to be limiting in any way.

When an optimal parameter value is identified by the iterative process (steps 504, 506 and 508 of FIG. 5), that parameter may be set (step 510) within the IMD 100 for continued application, or the value may be processed in other ways. In an equivalent embodiment of process 500, application of the response (i.e. steps 502 and 508) may be manually provided by a health care clinician or another source external to IMD 100, while monitoring functions (step 504) continue to be provided by IMD 100.

Accordingly, various methods and apparatus for diagnosing and gauging cardiac condition using potentiation are provided. While exemplary embodiments have been presented in the foregoing detailed description of the invention, it should be appreciated that a vast number of variations exist. It should also be appreciated that these exemplary embodiments are only examples, and are not intended to limit the scope, applicability, or configuration of the invention in any way. Rather, the foregoing detailed description will provide a convenient road map for implementing an exemplary embodiment of the invention. Various changes may be made in the function and arrangement of elements described in an exemplary embodiment without departing from the scope of the invention as set forth in the appended claims and their legal equivalents.

What is claimed is:

1. A method of improving a ventricular contractile status of a patient with an implantable medical device, the method comprising the steps of:

observing a cardiac perturbation of a patient during a first cardiac cycle, wherein said cardiac perturbation comprises one of an extra-systole and a premature contraction of a cardiac chamber;

measuring heart beat potentiation of the cardiac perturbation for at least one subsequent cardiac cycle;

quantifying the measured heart beat potentiation to determine the ventricular contractile status of the patient; and providing a response from the implantable medical device to the patient as a function of the quantified ventricular contractile status.

2. The method of claim 1 wherein the observing step further comprises inducing the cardiac perturbation in the patient via a cardiac pacing stimulus delivered from an implantable medical device.

3. The method of claim 2 wherein the cardiac perturbation comprises a premature ventricular contraction.

4. The method of claim 2 wherein the cardiac perturbation comprises an extra-systolic atrial beat.

5. The method of claim 2 wherein the cardiac perturbation comprises a change in heart rate induced via delivery of the cardiac pacing stimulus.

6. The method of claim 2 wherein the cardiac perturbation further comprises a change in hemodynamic pressure.

7. The method of claim 1 wherein the quantifying step comprises calculating a recirculation fraction as a function of the heart beat potentiation for the at least one subsequent cardiac cycle.

8. The method of claim 1 wherein the quantifying step comprises calculating a potentiation ratio as a function of the heart beat potentiation for the at east one subsequent cardiac cycle.

9. The method of claim 1 wherein the quantifying step comprises calculating a potentiation ratio and a recirculation fraction as a function of the heart beat potentiation for the at least one subsequent cardiac cycle.

10. The method of claim 1 wherein the response comprises providing a medication to the patient.

11. The method of claim 1 wherein the response comprises providing an electrical signal to the heart.

12. The method of claim 1 wherein the response comprises neurological stimulation to the patient.

13. The method of claim 1 wherein the response comprises adjusting a timing parameter.

14. The method of claim 1 wherein the response comprises storing data about the hemodynamic status in the implantable medical device.

15. The method of claim 1 further comprising the steps of gathering feedback data about the heart as the response is provided, and adjusting the response as a function of the feedback data.

16. The method of claim 15 wherein the response comprises providing a medication to the patient.

17. The method of claim 15 wherein the response comprises adjusting a timing parameter.

18. A method of improving a ventricular contractile status of a patient with an implantable medical device, the method comprising the steps of:
    producing an extra-systolic beat from an implantable medical device during a first cardiac cycle;
    measuring potentiation in a ventricular force interval resulting from the extra-systolic beat during at east one subsequent cardiac cycle;
    quantifying the potentiation in the ventricular force interval to determine the ventricular contractile status of the patient; and
    adjusting a parameter of a stimulus provided by the implantable medical device to the patient as a function of the determined ventricular contractile status.

19. A medical device configured to be implanted in a patient, the device comprising:
    a data collection module configured to identify contractile potentiation in the patient following a cardiac perturbation for a first cardiac cycle;
    a data processing module in communication with the data collection module, wherein the data processing module is configured to correlate the contractile potentiation to a hemodynamic status of the patient for at least one subsequent cardiac cycle; and
    a response module in communication with the data processing module, wherein the response module is configured to provide a response based upon the correlated hemodynamic status.

20. The device of claim 19 further comprising a digital memory in communication with the data processing module, and wherein the response further comprises storing historical data about the hemodynamic status in the digital memory.

21. The device of claim 19 wherein the response module comprises an interface to at least one pacing electrode.

22. The device of claim 21 wherein the data processing module is further configured to induce the perturbation in the patient using the at least one pacing electrode.

23. The device of claim 19 wherein the data processing module is further configured to adjust the response as a function of the response.

24. The device of claim 23 wherein the response comprises administering a drug therapy to a patient.

25. The device of claim 23 wherein the response comprises adjusting a pacing parameter.

26. A medical device implanted in a patient, the method comprising the steps of:
    means for observing a cardiac perturbation of a patient for a first cardiac cycle;
    means for measuring potentiation in ventricular force resulting from the cardiac perturbation during at least one subsequent cardiac cycle;
    means for quantifying the potentiation to determine a hemodynamic status of the patient; and
    means for providing a response to the patient as a function of the hemodynamic status of the patient.

27. The medical device of claim 26 further comprising means for inducing the cardiac perturbation in the patient from the implantable medical device.

28. A method of calibrating a parameter using an implantable medical device, the method comprising the steps of:
    providing a cardiac perturbation to a patient from an implantable medical device using an initial value of the parameter during a first cardiac cycle;
    observing contractile potentiation in the patient as a result of the cardiac perturbation for at east one subsequent cardiac cycle;
    adjusting a value of the parameter in response to the observed contractile potentiation; and
    repeating the adjusting and observing steps until a maximum amount of contractile potentiation is observed in the patient.

29. The method of claim 28 further comprising the step of setting an optimal value for the parameter, wherein the optimal value corresponds to the value used to generate the maximum amount of contractile potentiation.

30. The method of claim 28 wherein the parameter is a pacing interval.

31. The method of claim 30 wherein the pacing interval is an AV pacing interval.

32. The method of claim 30 wherein the pacing interval is a VV pacing interval.

33. The method of claim 29 wherein the parameter is a drug therapy.

34. The method of claim 29 wherein the parameter is a neurotherapy.

35. The method of claim 28 wherein the cardiac perturbation comprises a premature ventricular contraction.

36. The method of claim 28 wherein the cardiac perturbation comprises a change in hemodynamic pressure.

37. The method of claim 28 wherein the cardiac perturbation comprises an extra-systolic beat.

* * * * *

UNITED STATES PATENT AND TRADEMARK OFFICE
CERTIFICATE OF CORRECTION

PATENT NO. : 7,130,684 B2 Page 1 of 1
APPLICATION NO. : 10/426730
DATED : October 31, 2006
INVENTOR(S) : Mulligan et al.

It is certified that error appears in the above-identified patent and that said Letters Patent is hereby corrected as shown below:

Column 12, line 58 please change "at east one" to --at least one--.

Signed and Sealed this

Second Day of October, 2007

JON W. DUDAS
*Director of the United States Patent and Trademark Office*